United States Patent
Dandamudi et al.

(10) Patent No.: US 11,446,486 B1
(45) Date of Patent: *Sep. 20, 2022

(54) MULTIELECTRODE MEDICAL LEAD

(71) Applicants: Gopi Dandamudi, Gig Harbor, WA (US); Terrell M. Williams, Brooklyn Park, MN (US)

(72) Inventors: Gopi Dandamudi, Gig Harbor, WA (US); Terrell M. Williams, Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/337,944

(22) Filed: Jun. 3, 2021

(51) Int. Cl.
*A61N 1/05* (2006.01)
*A61N 1/375* (2006.01)
*A61N 1/362* (2006.01)

(52) U.S. Cl.
CPC .......... *A61N 1/0573* (2013.01); *A61N 1/362* (2013.01); *A61N 1/37512* (2017.08); *A61N 2001/058* (2013.01)

(58) Field of Classification Search
CPC .. A61N 1/0573; A61N 1/37512; A61N 1/362; A61N 2001/058
See application file for complete search history.

(56) References Cited

U.S. PATENT DOCUMENTS

| | | |
|---|---|---|
| 4,991,578 A | 2/1991 | Cohen |
| 5,246,014 A | 9/1993 | Williams et al. |
| 5,306,263 A | 4/1994 | Voda |
| 5,476,497 A * | 12/1995 | Mower ............... A61N 1/05 607/122 |
| 5,617,854 A | 4/1997 | Munsif |
| 5,772,693 A | 6/1998 | Brownlee |
| 5,851,226 A | 12/1998 | Skubitz et al. |
| 5,876,385 A | 3/1999 | Ikari et al. |
| 5,964,795 A * | 10/1999 | McVenes ............. A61N 1/056 607/122 |
| 5,987,746 A | 11/1999 | Williams |
| 6,004,280 A | 12/1999 | Buck et al. |
| 6,066,126 A | 5/2000 | Li et al. |

(Continued)

OTHER PUBLICATIONS

Kawashima et al., A macroscopic anatomical investigation of atrio-ventricular bundle locational variation relative to the membranous part of the ventricular septum in elderly human hearts, Surgical & Radiologic Anatomy, Feb. 19, 2005, pp. 206-213, vol. 27, Springer-Verlag, Heidelberg, Germany.

(Continued)

*Primary Examiner* — Eric D. Bertram
(74) *Attorney, Agent, or Firm* — Lund IP, PLLC

(57) ABSTRACT

A medical lead includes a lead body, a proximal connector, a helix extending from a distal end of the lead body. The helix is configured to anchor to a patient tissue, and the helix forms a helical electrode. The medical lead further includes a distal ring electrode, and a cable within the lead body, the cable including a cable conductor, a cable electrode proximate a distal end of the cable conductor, and a blunt dissection tip at a distal end of the cable. The cable is slidable within the lead body to extend and retract the cable electrode along a trajectory extending from the distal end of the lead body. When the helix is anchored to the patient tissue, the blunt dissection tip is configured to blunt dissect the patient tissue along the trajectory extending from the distal end of the lead body through extension of the cable.

31 Claims, 9 Drawing Sheets

(56) References Cited

U.S. PATENT DOCUMENTS

| | | | |
|---|---|---|---|
| 6,214,016 B1 | 4/2001 | Williams et al. | |
| 6,366,819 B1* | 4/2002 | Stokes | A61N 1/0565 |
| | | | 607/119 |
| 6,408,214 B1 | 6/2002 | Williams et al. | |
| 6,931,286 B2* | 8/2005 | Sigg | A61M 25/0084 |
| | | | 607/126 |
| 6,937,897 B2 | 8/2005 | Min et al. | |
| 7,056,294 B2 | 6/2006 | Khairkhahan et al. | |
| 7,082,335 B2 | 7/2006 | Klein et al. | |
| 7,177,704 B2 | 2/2007 | Laske et al. | |
| 7,647,124 B2 | 1/2010 | Williams | |
| 7,657,325 B2 | 2/2010 | Williams | |
| 7,729,782 B2 | 6/2010 | Williams et al. | |
| 8,100,883 B1 | 1/2012 | Johnson | |
| 8,332,042 B2 | 12/2012 | Williams | |
| 8,406,899 B2 | 3/2013 | Reddy et al. | |
| 8,606,369 B2 | 12/2013 | Williams et al. | |
| 8,620,433 B2 | 12/2013 | Ghosh et al. | |
| 8,744,579 B2 | 6/2014 | Parikh et al. | |
| 9,504,801 B2 | 11/2016 | Dangoisse | |
| 9,579,501 B2 | 2/2017 | Shuros et al. | |
| 9,662,501 B2 | 5/2017 | Mongeon et al. | |
| 9,700,729 B2 | 7/2017 | Ghosh et al. | |
| 10,737,097 B2 | 8/2020 | Williams et al. | |
| 10,773,087 B1 | 9/2020 | Williams et al. | |
| RE48,319 E | 11/2020 | Sambelashvili | |
| 10,888,354 B2 | 1/2021 | Kugler et al. | |
| 11,253,699 B1* | 2/2022 | Williams | A61N 1/0573 |
| 2003/0130713 A1 | 7/2003 | Stewart et al. | |
| 2004/0064158 A1* | 4/2004 | Klein | A61N 1/056 |
| | | | 607/9 |
| 2009/0105724 A1 | 4/2009 | Yoshizaki et al. | |
| 2014/0046389 A1* | 2/2014 | Anderson | A61N 1/0573 |
| | | | 607/4 |
| 2019/0321625 A1* | 10/2019 | Shuros | A61N 1/0573 |
| 2020/0114146 A1* | 4/2020 | Foster | A61N 1/362 |
| 2020/0261734 A1* | 8/2020 | Yang | A61N 1/056 |

OTHER PUBLICATIONS

Medtronic, C315 Catheter: For the SelectSecure® Pacing lead system, Dec. 2008, Medtronic, Inc., Minneapolis, Minnesota.

Medtronic, HIS—Bundle Pacing Introductory Tutorial, May 2017, Medtronic, Inc., Minneapolis, Minnesota.

Abdelrahman et al., Clinical Outcomes of His Bundle Pacing Compared to Right Ventricular Pacing, JACC vol. 71, No. 20, May 22, 2018, pp. 2319-2330, The American College of Cardiology Foundation, Washington, DC.

Vijayaraman et al., Prospective evaluation of feasibility and electrophysiologic and echocardiographic characteristics of left bundle branch area pacing, Heart Rhythm vol. 16, No. 12, Dec. 2019, pp. 1774-1782, Heart Rhythm Society, Washington, DC.

Williams et al., Cardiac Pacing Lead, Lund IP Docket No. 1004-001US01, U.S. Appl. No. 16/826,007, filed Mar. 20, 2020.

\* cited by examiner

MULTIELECTRODE MEDICAL LEAD

TECHNICAL FIELD

This disclosure relates to cardiac pacing.

BACKGROUND

Typically, pacing leads are deployed to various locations in the heart depending on the nature of the heart condition necessitating the pacing procedure. Conventional ventricular pacing typically involves implanting a lead at the apex of the right ventricle. This placement is still often utilized today even in the face of published evidence of the deleterious effects of bypassing the His/Purkinje system, otherwise known as the cardiac conduction system.

Pacemaker lead electrodes have been regularly placed in or on the heart in a position that bypasses the His/Purkinje system since the inception of pacing in 1957. Conventional pacing directly stimulates the myocardium and has been the standard of care even though His bundle pacing has been known and tried occasionally.

During and around the 1980s, scientific studies found that over time, ventricular pacing resulted in what was termed, "ventricular remodeling," which can result in a number of detrimental effects including: myofiber disarray, fatty tissue and fibrotic deposits away from the electrode, impaired endothelium function, acute hemodynamic compromise, redistribution of myocardial fiber strain and blood flow, with hypertrophy away from the electrode, mitral valve regurgitation due to poor papillary muscle timing, cardiac sympathetic activity, decreases in left ventricle (LV) chamber efficiency, slowing of LV isovolumic relaxation, far LV wall contracting against a closed aortic valve, tricuspid valve insufficiency due to lead mechanical disruption, and mitochondrial abnormality away from the electrode.

By 2002, large, controlled studies found that conventional ventricular pacing also resulted in heart failure hospitalization and mortality, especially when the patient was paced forty percent or more or the time. This iatrogenic problem is referred to as "pacing induced heart failure."

In spite of significant research demonstrating significant mortality reductions for His bundle pacing compared to conventional pacing, the value of His pacing has not been widely recognized or practiced among clinicians responsible for implanting cardiac pacing leads and pacemakers.

BRIEF SUMMARY

The inventors believe the limited prevalence of His bundle pacing, and when required, pacing the left bundle branch (LBB) of the conduction system, is in part due to lack of effective leads and lead delivery systems. The His bundle consists of two discreet bundles which separate at the crest of the ventricular septum to form the LBB and right bundle branch (RBB). The cardiac conduction system is comprised in part of His bundle which resides between the atrioventricular (AV) node, and the bifurcation of the LBB and RBB. These anatomic locations are regarded as difficult targets to reach.

For example, many patients cannot have LBB block corrected by His bundle pacing but can benefit from LBB pacing. Techniques disclosed herein facilitate both His bundle pacing, generally via the septal wall of the right atrium, and LBB pacing, generally via right ventricle (RV) septal access. The present disclosure describes examples of leads and methods for use including delivering a pacing lead to the LBB, at the septal wall of the RV or the His bundle in the right atrium.

Examples of the present disclosure includes a lead with a distal helix to facilitate anchoring to the septal wall of the RV proximate the RBB or, alternatively, proximate the His bundle, generally via the septal wall of the right atrium. Such leads may further include a blunt dissection electrode configured for deployment within the septum. The blunt dissection electrode may be advanced to the His bundle or LBB following anchoring the distal end of the lead into the septal wall with the helix. The lead further includes a second deployed electrode, such as helical electrode included in the distal helix. The second electrode may be used to capture the RBB while the first electrode captures the LBB. In this manner, examples of the disclosed lead facilitate targeting both the RBB and the LBB with a single lead, e.g., with bifocal stimulation or for cardiac resynchronization.

The lead may be implanted via a catheter. Implantation techniques may include selecting a trajectory for the blunt dissention electrode by manipulating the catheter after anchoring the helix to the septal wall. For example, with the distal end of the catheter-lead assembly anchored to the septal wall, the direction of the trajectory of the blunt dissection electrode may be selected by the clinician by bending the catheter through pushing and pulling from a proximal location outside the body of the patient, as well by rotating the catheter from the outside the body of the patient.

In one example, this disclosure is directed to a medical lead including a lead body, a connector proximate to a proximal end of the lead body, a helix extending from a distal end of the lead body. The helix is configured to anchor to a patient tissue, and the helix forms a helical electrode. The medical lead further includes a ring electrode proximate to the distal end of the lead body, and a cable within the lead body, the cable including a cable conductor, a cable electrode proximate a distal end of the cable conductor, and a blunt dissection tip at a distal end of the cable. The cable is slidable within the lead body to extend and retract the cable electrode along a trajectory extending from the distal end of the lead body. When the helix is anchored to the patient tissue, the blunt dissection tip is configured to blunt dissect the patient tissue along the trajectory extending from the distal end of the lead body through extension of the cable.

In another example, this disclosure is directed to a method for implanting a medical lead the medical lead including, a lead body, a connector proximate to a proximal end of the lead body, a helix extending from a distal end of the lead body, wherein the helix is configured to anchor to a patient tissue, and wherein the helix forms a helical electrode, a ring electrode proximate to the distal end of the lead body, a cable within the lead body, the cable including a cable conductor, a cable electrode proximate a distal end of the cable conductor, and a blunt dissection tip at a distal end of the cable. The cable is slidable within the lead body to extend and retract the cable electrode along a trajectory extending from the distal end of the lead body. The method includes securing the helix of to a patient tissue proximate a target site and extending the cable conductor from the lead body to deploy the cable electrode within the patient tissue.

In a further example, this disclosure is directed to a medical lead including a lead body, a connector proximate to a proximal end of the lead body, a helix extending from a distal end of the lead body, wherein the helix is configured to anchor to a patient tissue, a ring electrode proximate to the distal end of the lead body, and a cable within the lead body, the cable including a cable conductor, a first cable electrode proximate a distal end of the cable conductor, a second cable electrode proximal the first cable electrode and a blunt dissection tip at a distal end of the cable. The cable is slidable within the lead body to extend and retract the first cable electrode and the second cable electrode along a trajectory extending from the distal end of the lead body. When the helix is anchored to the patient tissue, the blunt dissection tip is configured to blunt dissect the patient tissue along the trajectory extending from the distal end of the lead body through extension of the cable.

DETAILED DESCRIPTION

Figure 1:
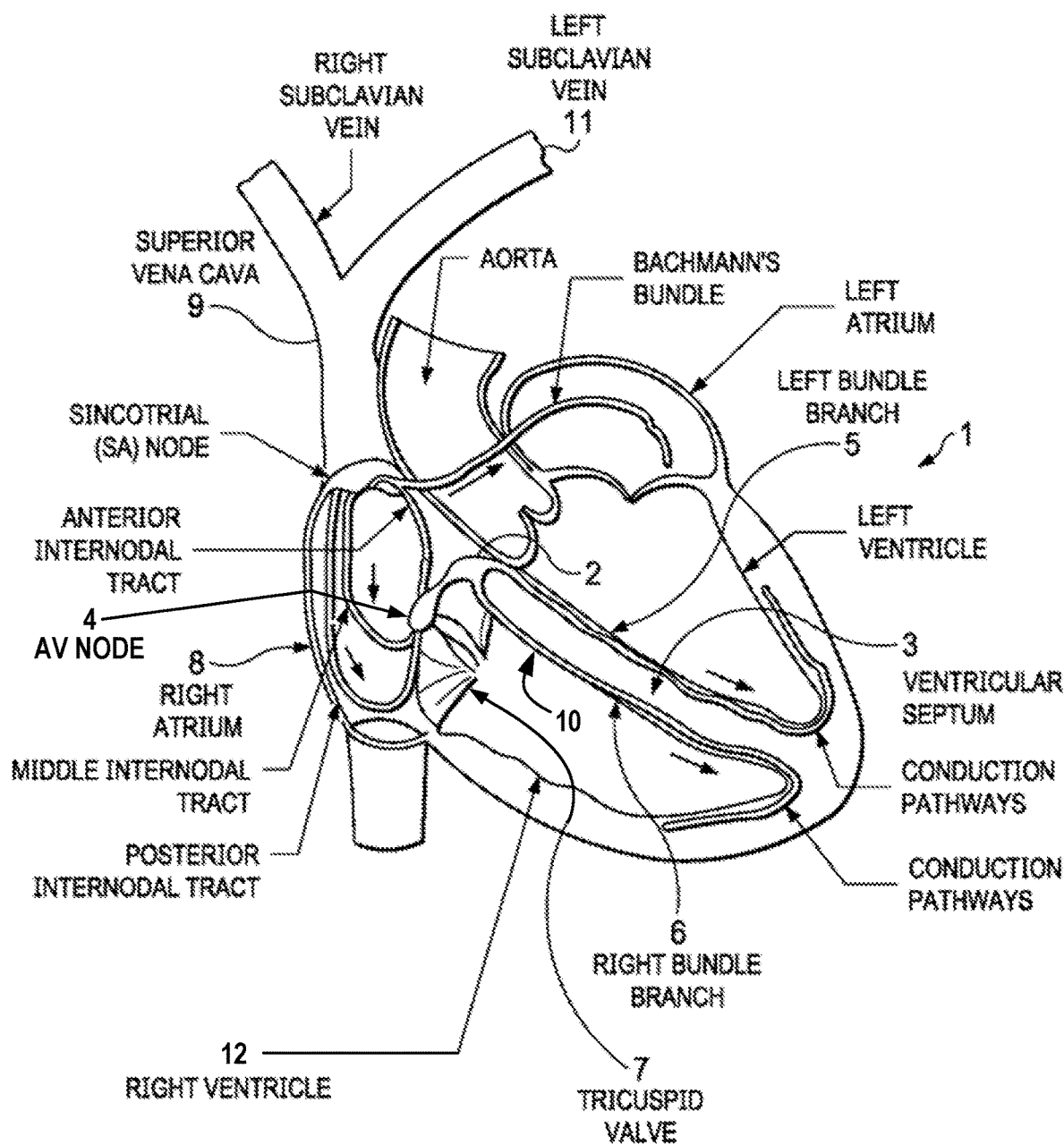
FIG. 1 is a cross-sectional illustration of a human heart depicting the anatomy of the heart and its electrical system.

The prevalence of His bundle pacing or LBB pacing, though increasing, is practiced in a small minority of pacing lead implantations both in the United States and worldwide. The His bundle and LBB present a small targets and are hard to reach successfully. This increases fluoroscopy or "flouro" time, which is a detriment to both patient and the surgical clinician. However, in one study by the inventors, the mortality rate of one hospital doing conventional pacing was compared with the mortality rate with another hospital doing pacing at the His bundle (for normal physiological ventricular activation). Heart failure and patient mortality was lower at the hospital providing physiological ventricular activation by His bundle pacing.

It is generally more difficult to place a cardiac lead electrode at the conduction system for His bundle pacing or LBB pacing than it is to place within the RV for conventional pacing. However, techniques of the present disclosure mitigate difficulties with locating a lead electrode to capture the His bundle or LBB. Locating a lead electrode to capture the LBB, which is important for patients with LBB block in which the capturing the His bundle may not provide effective LBB normalization. Disclosed techniques also facilitate capturing the RBB, e.g., for bifocal stimulation and/or to facilitate cardiac resynchronization.

In one example, a lead includes an anode ring electrode, and a helical electrode anchor configured to be anchored on the septum of the right atrium, piercing the endocardial membrane of the right atrium. The helical electrode may capture the RBB. A blunt dissection electrode is connected via a cable conductor extending from the connector end of the lead. A clinician advances the cable conductor through the coaxial center of the lead, advancing the blunt dissection electrode via the pierced endocardial membrane of the RV to a targeted portion of the cardiac conduction system, usually the His bundle within the septum or extending distally to the LBB.

The trajectory of the blunt dissection electrode is controlled by the angle of the lead delivery catheter following anchoring of the helical electrode anchor. While anchored, the clinician may manipulate the angle of lead delivery catheter. The catheter pivots the helical electrode, controlling the trajectory of the blunt dissection electrode.

In this manner, the catheter and fixation screw need not be presented at any particular angle (such as perpendicular) to the endocardial surface. The trajectory of the blunt dissection electrode can be manipulated after helical electrode fixation and has no bearing on His pacing threshold. Thus, a variety of lead delivery catheters may be suitable for delivery of leads disclosed herein.

Once the clinician is satisfied with the angle of the catheter, the clinician advances the cable, having the blunt dissection electrode attached at the distal tip, is advanced from the connector end, through the lead body and helical electrode to the targeted portion of the cardiac conduction system, e.g., via blunt dissection. In other examples, the tissue may be cut with a sharp electrode or RF energy. However, blunt dissection may provide an advantage of mitigating the risk of piercing the septum as the endocardial membrane of the ventricular septum provides a relatively durable and elastic layer resistant to blunt dissection compared to the muscular central portion of the ventricular septum.

Selection of either specific or nonspecific His bundle pacing can be achieved for type two His anatomy because of the blunt dissection electrode is small enough to fit within the His bundle. Type two His anatomy, existing in an estimated 32% of patients, is where the His bundle dives below the central fibrous body and is surrounded by myocardium. Large electrodes, such as helical electrodes of current leads may be too large to exclude the myocardium from activation along with the His bundle (called nonspecific His bundle pacing). In contrast, smaller electrodes of leads disclosed herein, such as those with an electrode radius of about 0.5 millimeters (mm), allow for "specific" His bundle pacing. Such smaller electrodes may also facilitate LBB pacing, in the event that LBB block cannot be corrected at the His bundle due to infra-hisian block, e.g., through transseptal lead placement.

In contrast, a clinician attempting to use a conventional screw-in lead meant for RV or atrial endocardial attachment may try to drill thru the septum—a process that is very tedious, reportedly requiring at times, forty turns, and having the risk of penetration into the lumen of the LV risking embolic stroke.

In examples where the helical electrode anchor includes a helical electrode, which facilitates targeting the RBB, either simultaneously or independently of the LBB, e.g., for cardiac resynchronization. The multiple electrode configuration of leads disclosed herein provide a number of options for stimulation of the His bundle, RBB and/or LBB. Moreover, stimulation parameters may be reprogrammed without further surgical intervention if needed to overcome post-implantation degradation of the hearts conduction system.

FIG. 1 shows the cardiac anatomy, especially the cardiac conduction system. In a healthy heart, the natural pacemaker, the SA node, activates the high conduction velocity Purkinje fibers within the right and left atria, resulting in coordinated atrial muscle cell contraction. This injects blood collected in the atria, into the powerful left and right ventricles. There is a pause in conduction at the AV node allowing the ventricles to fill. Then, just before blood flows back into the atria, the AV node activates the His bundle and, by high conduction velocity, the left and right bundle branches and the entire Purkinje system. This choreographs ventricular contraction, endocardial myocardium contracting first followed by epicardial muscle contraction. This programmed ventricular muscle activation produces an efficient pumping action that not only squeezes blood out of the ventricles but produces kinetic energy as blood is accelerated from the ventricles. The result of conventional pacing is compromised Hemodynamics due to slow cell-to-cell conduction and an aberrant ventricular activation sequence as the cardiac conduction system is bypassed. The far-left ventricular wall away from the electrode site has been seen contracting against an already closed aortic valve.

For contextual understanding of how examples of the disclosure are intended to function, FIG. 1 is included to illustrate the structure of a typical human heart 1 with relevant anatomical features shown. As mentioned, one example of the disclosure is directed to a method for deploying an electrical lead to the LBB 5, potentially accessed from target site 10 on ventricular septum 3 from within the RV 12. Such a target site 10 for proper deployment of a pacing lead, is depicted in FIG. 1 against the wall of ventricular septum 3 below tricuspid valve septal leaflet 7 within RV 12. Targeting LBB 5 is particularly useful for patients experience LBB block. Examples may simultaneously target the LBB and RBB to facilitate dual bipolar, dual unipolar pacing, and/or cardiac resynchronization therapy. Nonspecific bundle branch pacing (conduction system and nearby myocardium) or contractile myocardium only pacing of either cathode may be appropriate in some cases.

In other examples, the target site may be the His bundle 2 at the septum 3 distal to the atrioventricular (AV) node 4, but proximal to the LBB 5 and the RBB 6. Such a target site for proper deployment of a pacing lead into the His bundle is at the crest of the ventricular septum 3 on the atrial aspect of the annulus of the tricuspid valve septal leaflet 7 within the right atrium 8.

Figure 2:
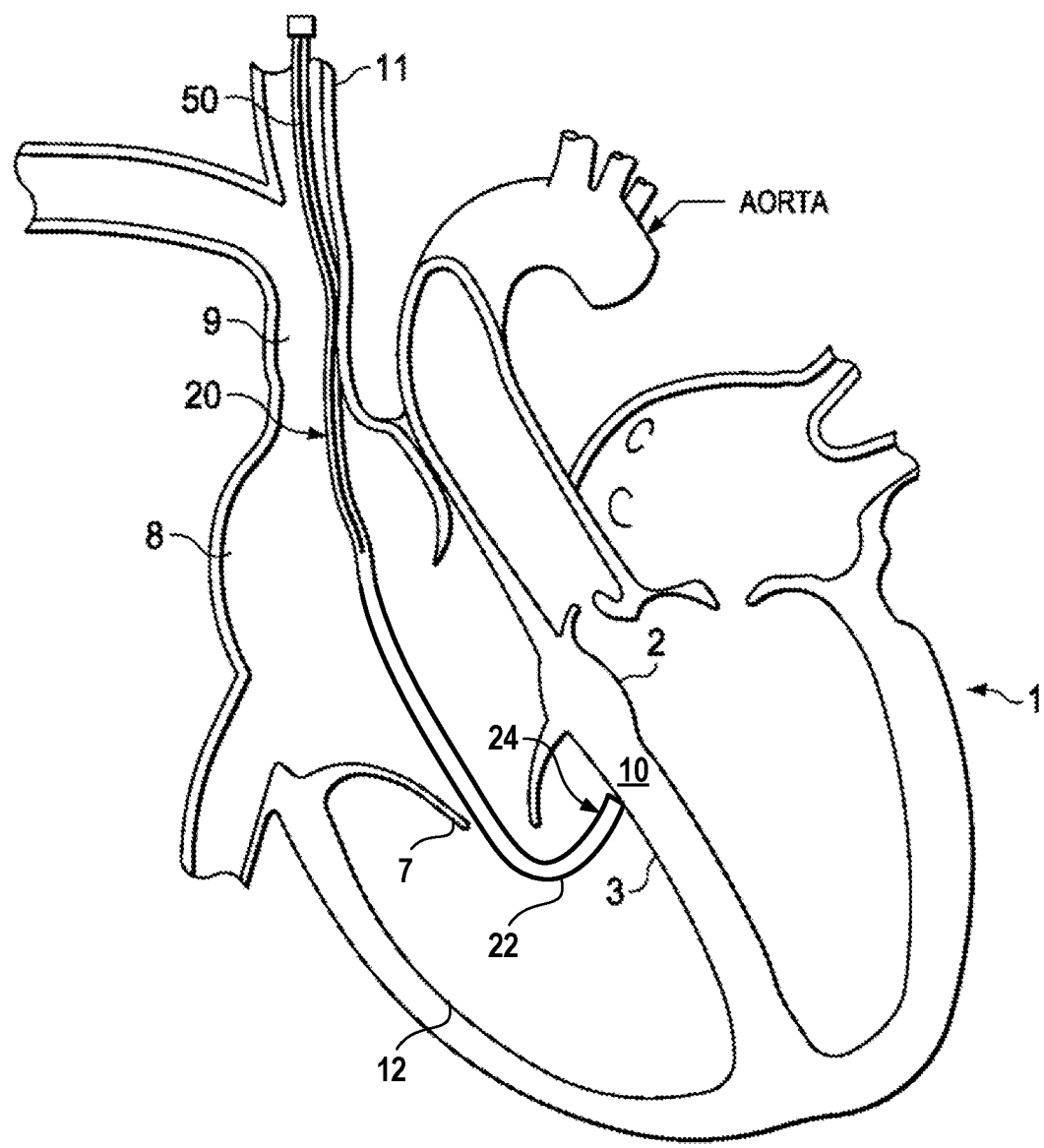
FIG. 2 is a cross-sectional illustration of a human heart wherein an example of a guide catheter is shown advanced to a target site within the RV corresponding to the RBB.

FIG. 2 is the schematic diagram of FIG. 1 in which a distal portion or end region 22 of delivery catheter 20 is shown extending into the RV 12 of the heart 1, from the superior vena cava 9 and the left subclavian vein 11, with the distal tip 24 positioned at the target site 10.

Typically, left pectoral side approach is desired. It involves accessing the heart via the left subclavian vein, the cephalic vein and more rarely the internal or external jugular vein, or femoral vein. However, it is also possible to utilize the less common right pectoral side approach. In either case, for catheter lead placement, a guide wire 50 may be advanced into the heart 1 from the access site. Delivery catheter 20 may be advanced through the vasculature and into the heart 1 over the guidewire; once in position the guidewire is removed. A pacing lead is then advanced through the guiding catheter 1 to be deployed at various regions in the heart.

Figure 3:
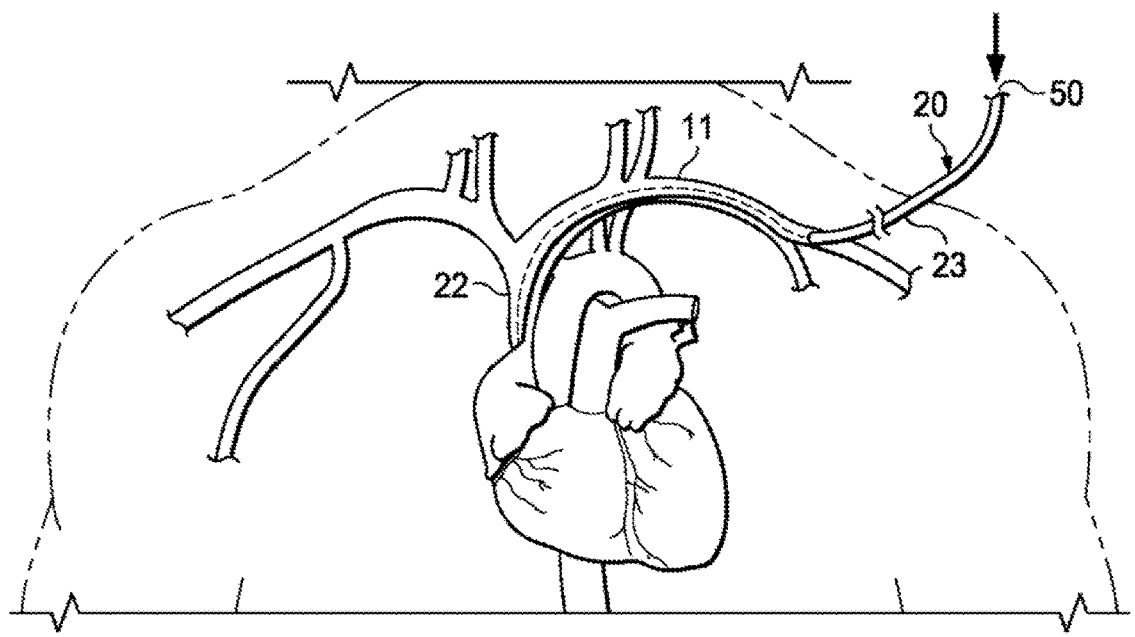
FIG. 3 is an anatomical illustration of a patient and the manner in which the example shown in FIG. 2 initially accesses the vasculature prior to advancement into the heart.

According to one method, a clinician positions guide wire 50 into the heart 1, for example via a "sub-clavian stick" or central venous access procedure such as is illustrated in FIG. 3. Accordingly, the catheter 20 is passed over the guide wire and advanced into the superior vena cava 9 from the left subclavian vein 11 through right atrium 8 and tricuspid valve septal leaflet 7 and into the RV 12 such as is in the manner shown in FIG. 2.

Figure 4:
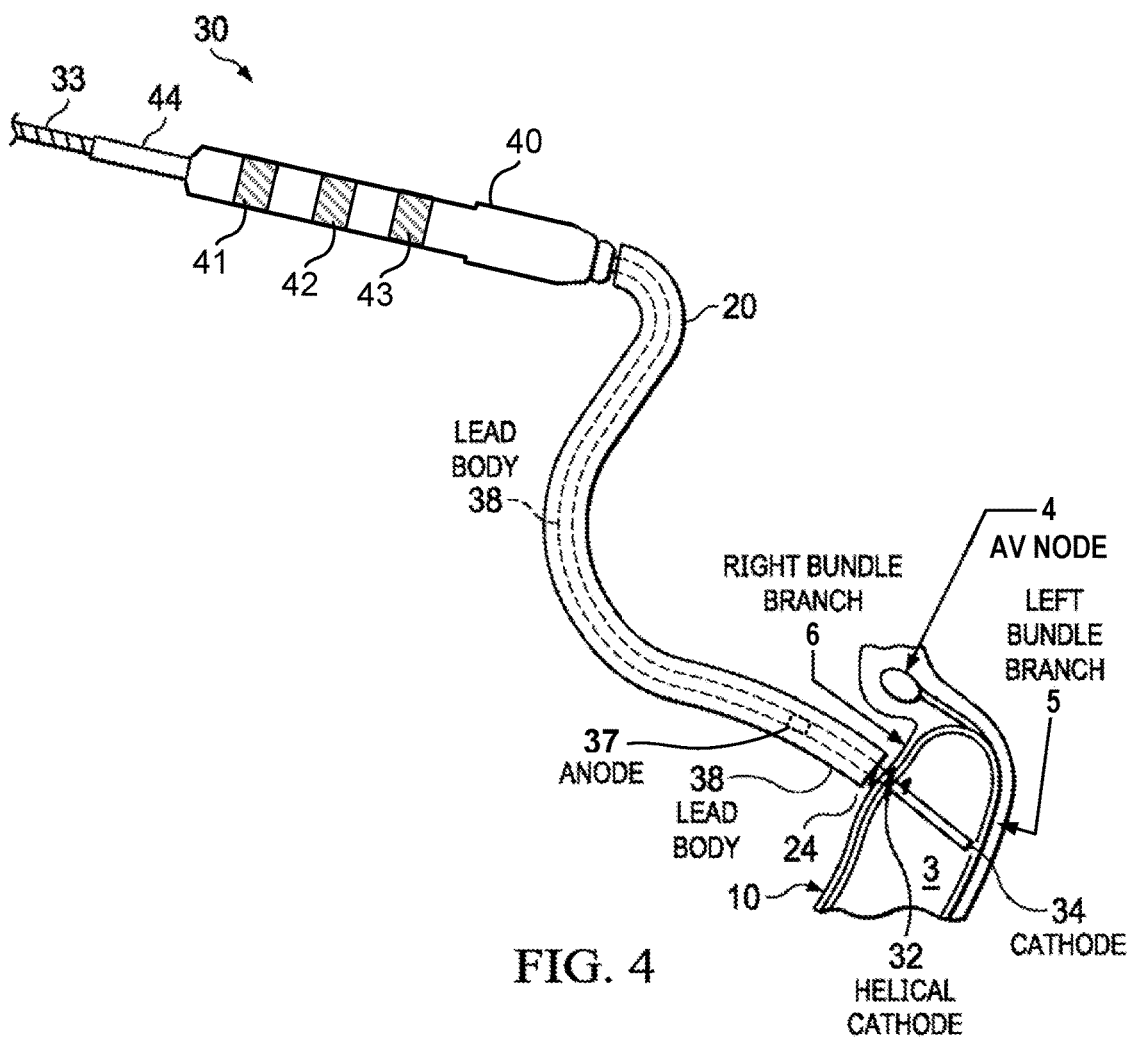
FIG. 4 is a conceptual illustration of a pacing lead accessing the septum from the RV in accordance with one example of this disclosure.

FIG. 4 illustrates a tripolar, or more specifically, a dual bipolar, medical electrical lead 30 in accordance with one example of this disclosure. Medical electrical lead 30 includes a helical electrode 32 and anode ring electrode 37, which are electrically coupled to connector terminals 41, 42. Medical electrical lead 30 further includes a central cable conductor 33 terminating at blunt dissection electrode 34 and extending within a central lumen of lead 30 about a length of lead body 38 for coupling to connector pin 44 of proximal connector 40.

Cable conductor 33 includes one or more conductive elements forming an electrical connection between blunt dissection electrode 34 and connector pin 44 once connector pin 44 is connected to the conductive elements of cable conductor 33. In various examples, cable conductor 33 may include a solid wire conductor, a stranded wire, or a coil conductor. In a particular example, cable conductor 33 may include a fiber core coil with one or more electrically conductive wires coiled on a fiber core. The fiber core may provide tensile strength for cable conductor 33 and mitigate stretching of the coiled conductors during retraction of cable conductor 33.

In the same or different examples, cable conductor 33 may be an insulated cable conductor including outer insulating layer, leaving the distal tip exposed for blunt dissection electrode 34. The insulating layer may include silicone rubber, polyurethane parylene, polymide and/or ethylene tetrafluoroethylene (ETFE) cable insulation. In some examples, connector pin 44 may be a self-stripping connector pin 44 to allow contact with the conductive elements of cable conductor 33. Alternatively, connector pin 44 may make electrical contact with conductive elements of cable conductor 33 upon tightening of a setscrew of the connector of a pulse generator or other device connected to proximal connector 40. Central cable conductor 33 is slidable the central lumen of lead body 38 to extend and retract blunt dissection electrode 34 relative to the distal end of lead body 38.

In the same or different examples, blunt dissection electrode 34 may be a unitary component with the conductive element(s) of cable conductor 33 or may be a separate component physically and electrically coupled to the distal end of the conductive element(s) of cable conductor 33, for example, by solder or welding, such as laser welding. Blunt dissection electrode 34 forms a rounded frontal surface extending across a width of the cable. In some examples, the blunt dissection electrode 34 is a 0.5 to 2.0 mm diameter, such as 0.7 to 1.0 mm diameter hemispherical electrode, such as a half sphere with a diameter of about 0.87 mm, at the end of an insulated blunt dissection electrode conductor of the same diameter in order to provide blunt dissection. In the same or different examples, the electrode proximate the distal end of cable conductor 33 may be a ring electrode instead of a tip electrode (such as electrode 535 of lead 530 in FIG. 11).

Medical electrical lead 30 includes a second conductor within lead body 38 extending between ring terminal 41 and anode ring electrode 37. Medical electrical lead 30 further includes a third conductor within lead body 38 extending between ring terminal 42 and helical electrode 32. In some examples, the second conductor and the third conductors are coaxial, insulated coil conductors surrounding the central cable conductor 33 within the lead body 38. The insulation should be selected to provide low friction with the central cable conductor 33. For example, the insulation of the coil conductors may be a low friction important polymer material, such as silicone rubber, polyurethane, parylene, polymide and/or ETFE or other non-conductive material. Likewise, central cable conductor 33 may be insulated with a low-friction material or include a low-friction coating, such as silicone rubber, polyurethane, parylene, polymide and/or ETFE.

Helical electrode 32 may be made from a wire, such as a platinum alloy or other biocompatible metal. The number of turns and length of the helix may be adapted for a particular application. For example, helical electrode 32 may have 1 to 8 turns, such as 2 to 4 turns to support adequate fixation within patient tissue. A septal thickness can be anywhere from 0.9 to 1.2 centimeters in normal individuals. A risk of perforation will likely go up if the helix is too long and the entire helix penetrates the septum. Accordingly, the dimensions of the helix should be selected to allow fixation and capture of the RBB but mitigate a risk of perforation. In the present example, a helix length of 1.0 to 8.0 mm may be appropriate to mitigate a risk of piecing the septum, such as a helix length of 1.5 to 4 mm, such as about 1.8 mm. As used herein, the term about means within a range of tolerances of manufacturing techniques used to produce the referenced element.

Anode ring electrode 37 is coplanar with an outer surface of lead body 38. The spacing and surface area of anode ring electrode 37 is selected to provide support stimulation via both helical electrode 32 and blunt dissection electrode 34. In some examples, anode ring electrode 37 may have a spacing of between 5 to 15 mm from helical electrode 32, such as a spacing of between 7 to 10 mm, such as a spacing of about 9 mm. In the same or different examples, anode ring electrode 37 may have a surface area of between 10 to 30 square mm, such as a surface area of between 15 to 20 square mm, such as a surface area of about 16.9 square mm.

In one particular example of lead 30, the following dimensions may be used. Lead body 38 diameter 3 to 6 French, such as about 4.1 French, cable conductor 33 diameter, 0.02 to 0.05 inches, such as about 0.028 inches, helical electrode 32 length 1 to 4 mm, such as about 1.8 mm, helical electrode 32 pitch, 0.5 to 2 mm, such as about 1 mm, helical electrode 32 wire diameter 0.1 to 1.0 mm, such as about 0.3 mm. In the same or different examples, a platinum alloy may be utilized for the helical electrode 32 wire such as Pt 80%/Ir 20% or Pt 90%/Ir 10% for a thinner wire.

As used herein, the terms anode and cathode merely represent example uses of particular lead electrodes. For example, anode ring electrode 37, helical electrode 32, and blunt dissection electrode 34 are electrically isolated within medical lead 30 such that such that any two of anode ring electrode 37, helical electrode 32, and blunt dissection electrode 34 may form an electrode pair to deliver stimulation. However, the polarity of the stimulation is controlled by a pulse generator and not inherent to the structure of electrical lead 30 itself. Thus, the pulse generator could reverse the polarity of anode ring electrode 37, helical electrode 32, and blunt dissection electrode 34, use any two electrodes as an anode-cathode pair, or even use one or more of anode ring electrode 37, helical electrode 32, and blunt dissection electrode 34 in a unipolar configuration in combination with the pulse generator housing.

In FIG. 4, a close-up view of the distal tip 24 of the catheter 20 is shown following advancement of medical electrical lead 30 though a lumen of the catheter 20 to the target site 10. In this example, the target site for blunt dissection electrode 34 is the LBB, although the His bundle can also be targeted.

The lead 30 is extended distally from catheter distal tip 24, exposing helical electrode 32. At this point, the clinician may map of the RBB with the helical electrode 32 evaluate capture threshold. If desired, the clinician may adjust the position of the distal tip 24 of the catheter 20 adjacent the septal wall to improve capture of the RBB before proceeding to anchor the helical electrode 32.

The lead 30 is anchored into the septum 3 by clockwise rotation of the lead body 38 targeting the RBB, so that helical electrode 32 screws through the endocardial membrane and into the septal wall. The clinician may again map of the RBB with the helical electrode 32 to confirm capture threshold. If desired, the clinician may adjust the position of helical electrode 32 within the septal wall to improve capture of the RBB before proceeding to extend blunt dissection electrode 34.

The blunt dissection electrode 34 is extended into the septum 3 to provide pacing to the heart 1 via the LBB. The blunt dissection electrode 34 punctures the endocardial membrane in the center of helical electrode 32. In some examples, cable conductor 33 and blunt dissection electrode 34 may enlarge the perforation in the endocardial membrane created by helical electrode 32. In other examples, cable conductor 33 may be withdrawn from lead body 38 and a needle or stylet (not shown) may be used to puncture the endocardial membrane. In further examples, RF energy may be applied to cable conductor 33 to cross the RV endocardium, then detaching the RF connection to cable conductor 33 and advance it to the LV endocardium. No matter the technique used to puncture the endocardial membrane, blunt dissection electrode 34 pushes through septal tissue using blunt dissection. With the blunt dissection electrode 34 targeting the LBB, the helical electrode 32 is proximate the RBB, facilitating cardiac resynchronization therapy by independently activating helical electrode 32 and blunt dissection electrode 34.

The use of a stylet or needle may be particularly advantages for puncturing tissues with more toughness than the septal wall within the right atrium. For example, if targeting the His bundle from the right ventricle, a stylet or needle may be used to penetrate the central fibrous body. In one contemplated example, a clinician may first target the His bundle from the septal wall within the right atrium.

While blunt dissection electrode 34 is the preferred configuration of cable conductor 33 for use in septal implantation, other configurations of cable conductor 33 are also possible, including a pointed tip instead of blunt dissection electrode 34.

Figure 5A:
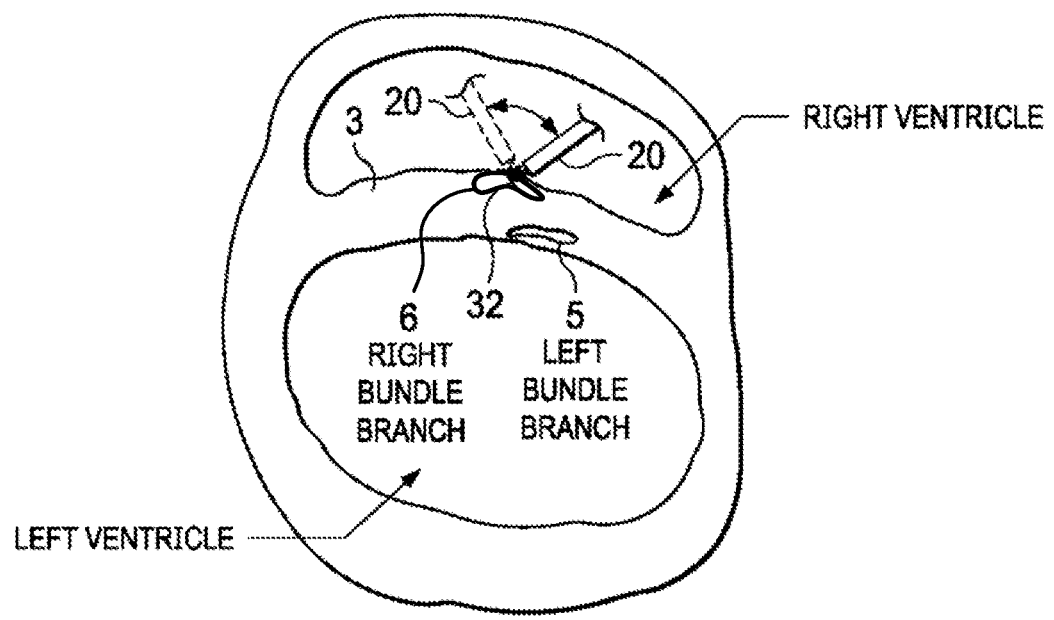
FIGS. 5A-5C illustrate detailed views of the distal region and tip of the pacing lead while mapping the LBB while attached to and fixed in a patient's septum.
Figure 5B:
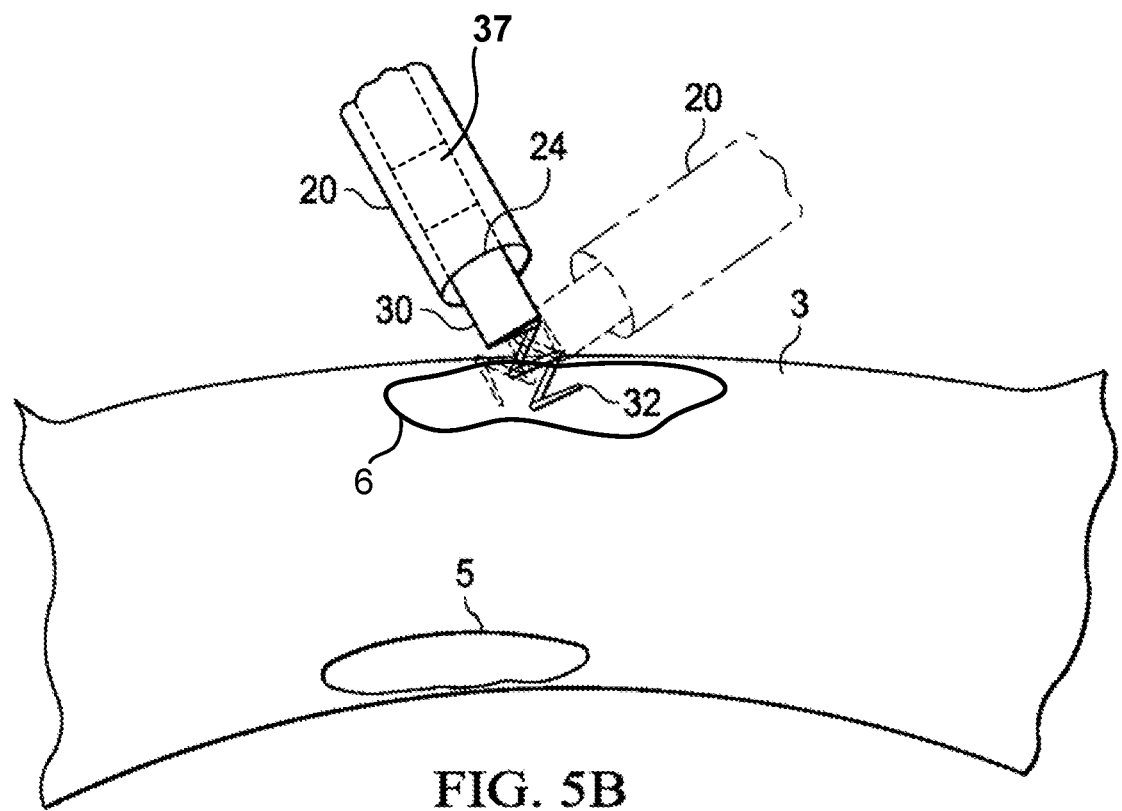
Figure 5C:
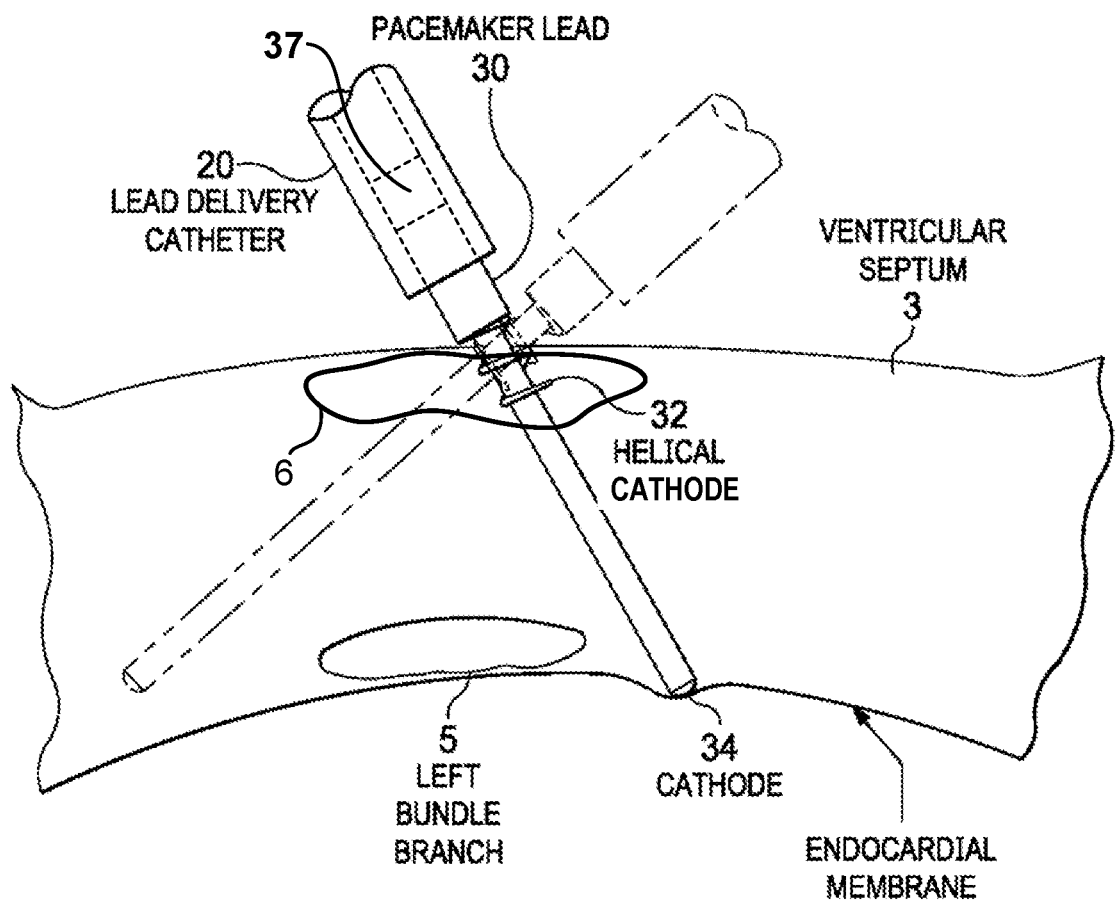

FIGS. 5A-5C illustrate detailed views of the distal region and tip of the pacing lead at a target site in a patient's septum. Specifically, FIG. 5A shows the trajectory of the blunt dissection electrode direction for mapping of the LBB during catheter introduction of the lead 30, while FIG. 5B shows a closeup of the lead delivery catheter and lead tip. The helical electrode 32 for lead attachment is shown anchored and is pivoted by the lead delivery catheter.

FIG. 5C shows the LBB mapping process and possible range of blunt dissection electrode location. Mapping for lead location is accomplished by sensing the LBB potential and/or pacing the LBB to produce a narrow QRS on the surface ECG, typical of physiologically normal ventricular activation. The trajectory of the blunt dissection electrode advancement is controlled by manipulation of the lead delivery catheter. Resistance to advancement of cable conductor 33 is felt when the electrode 34 impinges on the tough left ventricular endocardial membrane. See the tenting effect of the opposite endocardial membrane in FIG. 5C.

Figure 6:
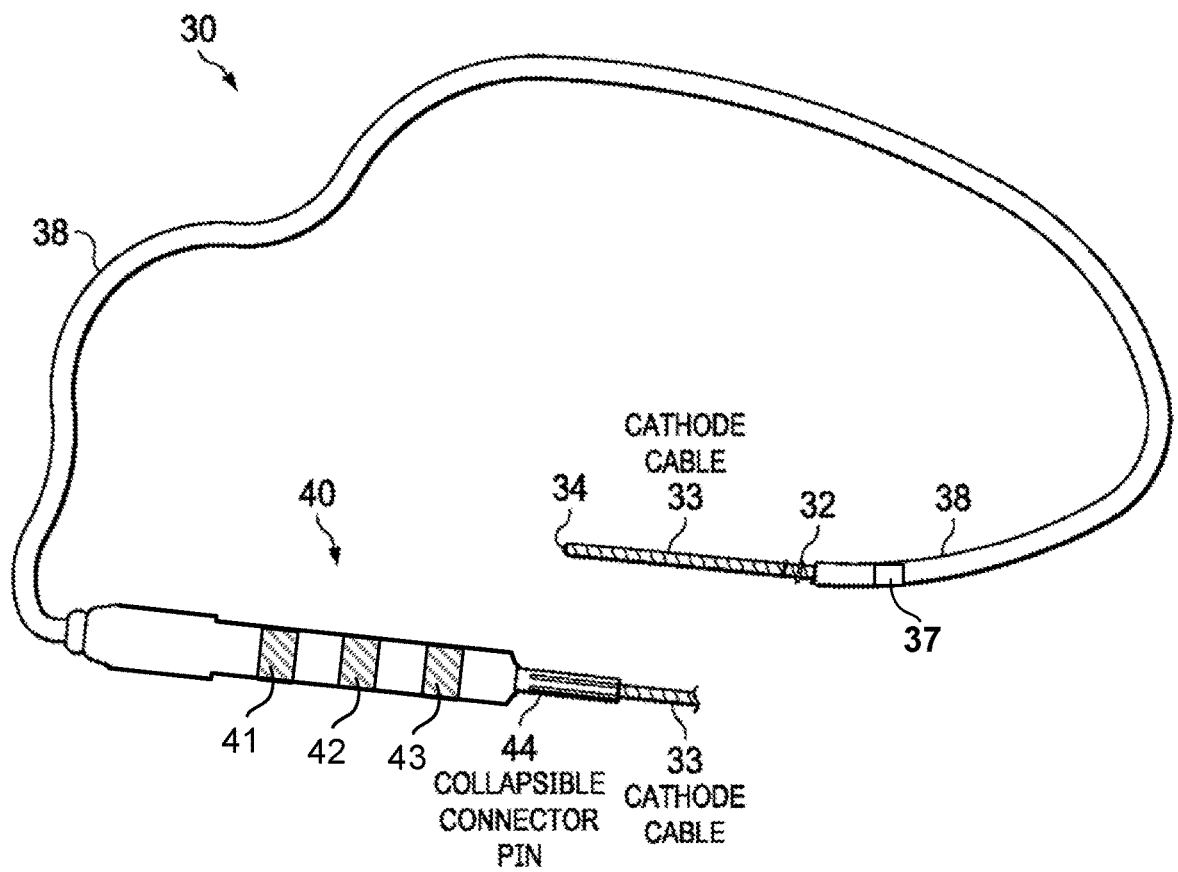
FIG. 6 illustrates the pacing lead with the proximal blunt dissection conductor and a self-stripping connector pin.

FIG. 6 illustrates lead 30 including a proximal connector 40 with a self-stripping connector pin 44. After selecting a proper lead position in the heart, cable conductor 33 is cut flush with the connector pin 44. The pulse generator's connector setscrew is tightened to make electrical contact, fracturing the cable insulation, and completing the circuit to blunt dissection electrode 34. The setscrew also fixes the relative position of cable conductor 33 to proximal connector 40. Also illustrated is proximal ring terminals 41, 42, 43 located adjacent and distal to connector pin 44. Ring terminal 41 provides an electrical connection to anode ring electrode 37, while ring terminal 42 provides an electrical connection to cathode electrode 32. Ring terminal 43 may provide a redundant connection to one of electrodes 34, 32, 37 or a connection to an optional fourth electrode (not shown), such as a second distal electrode on lead body 38, either proximal or distal to electrode 37.

In other examples, a proximal end of cable conductor 33 may include an exposed conductor the same diameter as the pin electrode of an IS-4 connector, or other industry standard connector. In such examples, the exposed conductor may simply be cut to the proper length after extending blunt dissection electrode 34 to the target site. In such examples, collapsible connector pin 44 is not required as the exposed proximal end of cable conductor 33 itself serves as the pin electrode of connector 40. The pulse generator's connector setscrew secures the position of cable conductor 33 relative to the connector body.

The example proximal connector 40 illustrated in FIG. 6 conforms to the IS-4 standard. In various examples, connector 40 may conform to a standard pulse generator connector, such as an IS-1, IS-4, DF-1, DF-4, or other industry standard connector.

Figure 7A:
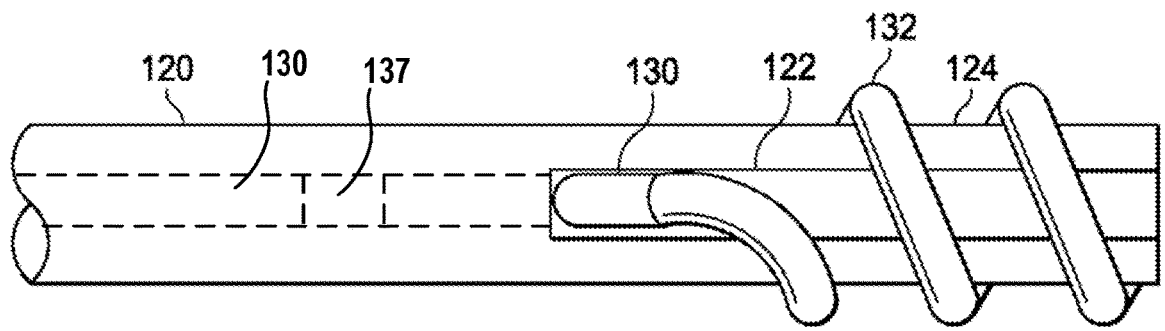
FIGS. 7A-7C illustrate an alternative lead design with an exposed helical electrode that facilitates mapping.
Figure 7B:
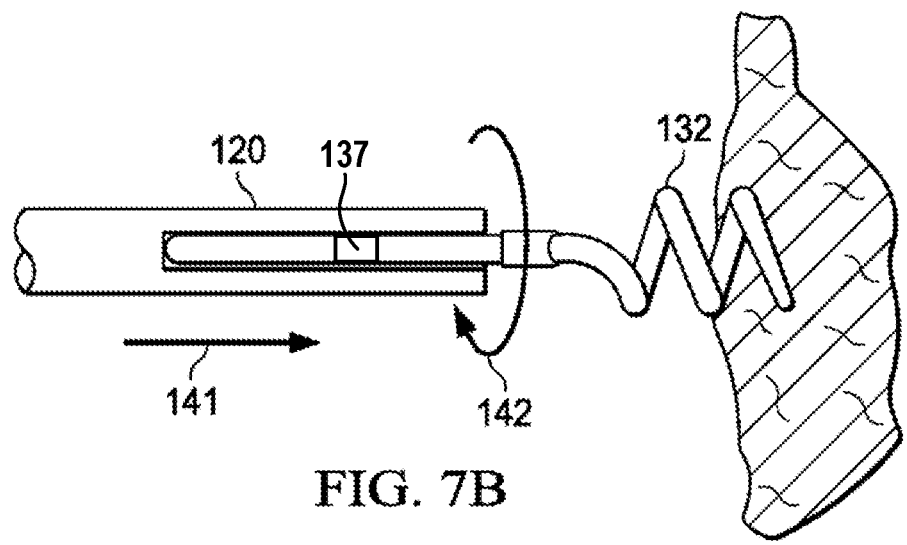
Figure 7C:
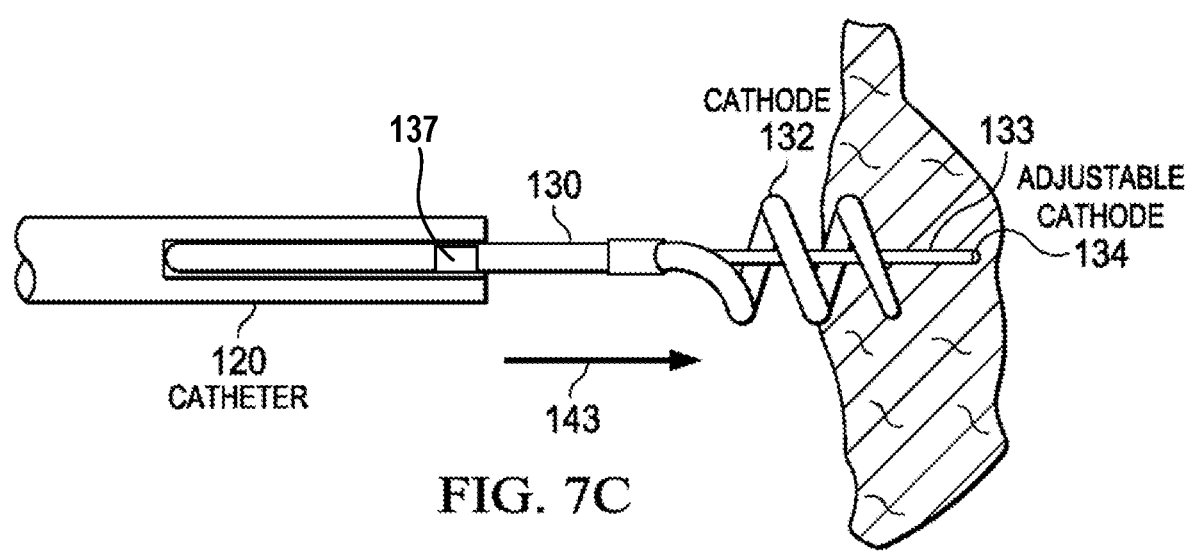

FIG. 7A-7C illustrate the distal end of a medical electrical lead 130, which provides an alternative lead design as compared to medical electrical lead 30. With this example, a helical electrode 132 is attached over the lead delivery catheter tip 124. This exposes the helical electrode 132 for mapping purposes. As shown in FIG. 7A, helical electrode 132 extends through slot 122 which extends along a length of delivery catheter 120 at lead delivery catheter tip 124. The pointed distal tip of helical electrode 132 is closely fitted to the catheter outer diameter to prevent snagging on intervascular tissue during venous passage of the catheter lead assembly. Deployment of helical electrode 132, e.g., through extension of cable conductor 133 in direction 141, then turning lead 130 relative to the patient tissue in direction 142 (corresponding to the curvature of helical electrode 132) anchors the distal tip of helical electrode 132 in the patient tissue.

Similar to lead 30, lead 130 includes an anode ring electrode 137. Lead 130 also includes a blunt dissection electrode 134, the trajectory of which is selectable by a clinician by manipulating the catheter lead assembly after anchoring helical electrode 132 within a tissue of the patient, such as the septal wall. This design of catheter 120 and lead 130 may increase the percutaneous introduction size, such as by 2 French as compared to catheter 20 and lead 30. Following the selection of the trajectory, the clinician may deploy electrode 134 within the patient tissue along direction 143, representing the selected trajectory, through extension of cable conductor 133 by pushing cable conductor 133 relative to helical electrode 132 of lead 130.

Figure 8:
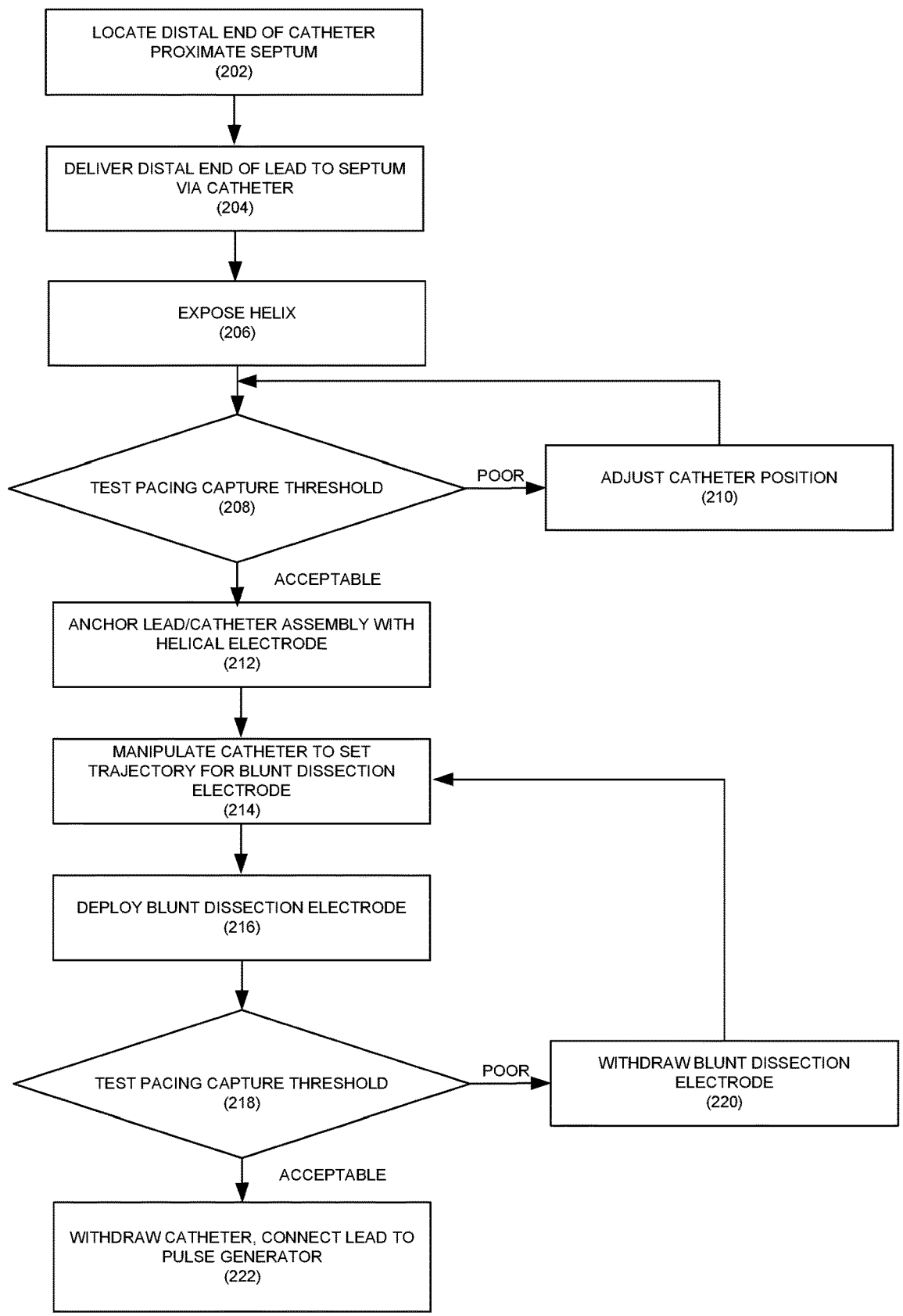
FIG. 8 is a flowchart illustrating techniques for locating a lead electrode proximate the LBB and RBB for cardiac resynchronization therapy.

FIG. 8 is a flowchart illustrating techniques for locating a lead electrode to pace the cardiac conduction system, to allow capture of both the RBB and LBB. For clarity, the techniques of FIG. 8 are described with respect to catheter 20 and medical electrical lead 30, although the techniques may likewise be applied to medical electrical leads 130, 330, 430, 530 and to variations of the example leads disclosed herein.

First, a clinician positions the distal tip 24 of catheter 20 at the target site 10 on a patient's septum within the RV (FIG. 8, step 202). In some example, a guidewire may be used to direct the catheter to target site 10. Once, the distal tip 24 of catheter 20 is positioned at the target site 10, the clinician removes guidewire (if any) and introduces lead 30 via the central lumen of the catheter 20. The distal end of lead 30 is delivered to the target site 10 in the septum via catheter 20 (FIG. 8, step 204). In other examples, lead 30 may be introduced with a stylet, after temporarily extracting the central cable conductor 33 from the central lumen of lead 30. The relatively stiff stylet may also be used by, blunt dissection, to clear a pathway through tough tissue such as the central fibrous body for His bundle pacing or along the left ventricular septum paralleling the LBB, especially when a relatively flexible cable conductor 33 is desirable.

For mapping, the clinician exposes the helical electrode 32 out the distal tip 24 of catheter 20 (FIG. 8, step 206). The clinician may test pacing capture threshold with helical electrode 32. For example, the clinician may test capture threshold of the RBB to find a suitable target site for the implantation. The clinician adjusts the location of the distal tip 24 of catheter 20 to select a target site for the implantation while testing pacing capture threshold with helical electrode 32 (FIG. 8, step 210).

The clinician anchors the catheter lead assembly to the target site 10 in the septum by rotating the lead 30 to engage the septum with the helical electrode 32 of lead 30 (FIG. 8, step 212). Preferably, to limit flouro time and trauma to patient tissue, helical electrode 32 is only anchored a single time, but the clinician may withdraw and anchor the helical electrode 32 if the pacing or sensing capture threshold is undesirable.

After securing the helix, the clinician may then manipulate the catheter 20 to set a desired trajectory for blunt dissection of the septum with the blunt dissection electrode blunt dissection electrode 34 (FIG. 8, step 214). For example, the clinician may select a trajectory for the blunt dissention electrode by manipulating the catheter after anchoring the helical electrode to the septal wall by bending the catheter through pushing and pulling from a proximal location outside the body of the patient, as well by rotating the catheter from the outside the body of the patient. Once helical electrode 32 is fixed to the septum, the septal wall is punctured and the blunt dissection electrode can be advanced, by blunt dissection between about 0.9 to 1.8 centimeters in an adult patient from the base of helical electrode 32, toward the LBB, just inside left ventricular septum (FIG. 8, step 216).

For mapping, the clinician may optionally withdraw the blunt dissection electrode 34 (FIG. 8, step 220), set a new desired trajectory, and redeploy the blunt dissection electrode 34. Generally, however, a clinician will only want to retract and redeploy the blunt dissection electrode 34 if sensing or pacing capture threshold is undesirable (FIG. 8, step 218). If mapping finds adjustment is necessary, blunt dissection electrode 34 is extracted to helical electrode 32 and helical electrode 32 can be pivoted to a desired new trajectory for advancement of cable conductor 33.

Examples may simultaneously target the LBB and RBB to facilitate dual bifocal, dual bipolar or unipolar pacing, for cardiac resynchronization therapy. Nonspecific bundle branch pacing (conduction system and nearby myocardium) or contractile myocardium only specific bundle branch pacing of either cathode may be appropriate in some cases.

Cathodal voltage stimulation of the LBB via blunt dissection electrode 34 and cathodal voltage stimulation of the RBB via helical electrode 32 can be independently adjusted to suit the LBB pacing voltage threshold and the RBB pacing voltage threshold independently to produce LV/RV synchrony. Alternatively, lead 30 may be operated to provide dual bifocal stimulation. In one example, the dual bifocal stimulation may operate ring electrode 37 as the anode and alternatively using blunt dissection electrode 34 and helical electrode 32 as cathodes. In another example, the dual bifocal stimulation may operate helical electrode 32 as the anode with and blunt dissection electrode 34 as the cathode alternated with operating ring electrode 37 as the anode with and helical electrode 32 as the cathode.

With His bundle, RBB and LBB pacing, pacing threshold voltage is generally greater than that of conventional pacing, but current threshold is generally less than that of the electrode of conventional pacing leads having higher electrode surface area, thus lower pacing impedance, so that the battery drain is comparable or better than with to conventional pacing. Blunt dissection electrode pacing impedance may be on the order of 1,000 ohms.

Blunt dissection electrode 34 forms a rounded frontal surface extending across a width of the cable. In some examples, the blunt dissection electrode 34 is a 0.7 to 1 mm diameter hemispherical electrode at the end of an insulated conductor of the same diameter in order to provide blunt dissection. This relatively small surface area (of about one square mm) for the exposed electrode may provide one or more advantages. For example, the smaller area may facilitate a reduced battery drain. Micro-dislodgement issues with other small pacing electrodes should be limited due to the embedded myocardial electrode placement of blunt dissection electrode 34 as opposed to placement on the endocardial surface as is the case for conventional tined leads. Thus, the disclosed techniques may mitigate instances of micro-dislodgement as can occur with electrodes positioned on the surface of a patient tissue.

In the same or different examples, the hemispherical tip electrode 34 of cable conductor 33 may be coated with a steroid to mitigate scar tissue and its negative effects on capture threshold over time.

While lead 30 may optionally be used to target the His bundle from the right atrium, occasionally, His bundle pacing (at the crest of the ventricular septum and within the right atrium) cannot correct LBB block. LBB block cannot be corrected by His bundle pacing in as many as 30-40% of patients due to infra-hisian block. When that happens, cable conductor 33 may be retracted and the trajectory of cable conductor 33 adjusted to target the LBB. Specifically, the clinician may target the LBB from with the right atrium without repositioning the anode helix, rather than from the RV as described previously. In such examples, the previously anchored anode helix can be pivoted about ninety degrees to align with the ventricular septum. When cable conductor 33 is advanced, blunt dissection electrode 34 slides along the endocardial membrane of the left ventricle, targeting the LBB, thereby bypassing the infra-hisian block.

When used for His pacing, particularly when the LBB block cannot be corrected at the His bundle due to distal block, blunt dissection electrode 34 is retracted. The catheter is rotated to a blunt dissection electrode trajectory that aims at the LBB. The blunt dissection electrode is then advanced along the left ventricular endocardial membrane to pace the LBB. In such examples, lead 30 may be used to apply bifocal stimulation to the LBB with electrode 34 and either of two electrodes 32, 37 or trifocal stimulation using all three electrodes 34, 32, 37. The blunt dissection tip mitigates the risk of puncturing the septal wall of the left ventricle. Such examples allow a clinician to first target the His bundle from the right atrium and adjust to the LBB if needed within limited flouro time.

Once the position of the blunt dissection electrode 34 is satisfactory, the clinician may withdraw catheter 20, cut the cable conductor 33 flush with connector pin 44, insert proximal connector 40 into the pulse generator's connector, and tighten the setscrew to cut through the insulation and complete the circuit (FIG. 8, step 222). In examples in which the pulse generator is an implantable pacemaker, the clinician then inserts the implantable pacemaker in a pocket under the skin in the patient's chest and is ready for sensing and/or pacing via the lead 30.

Figure 9:
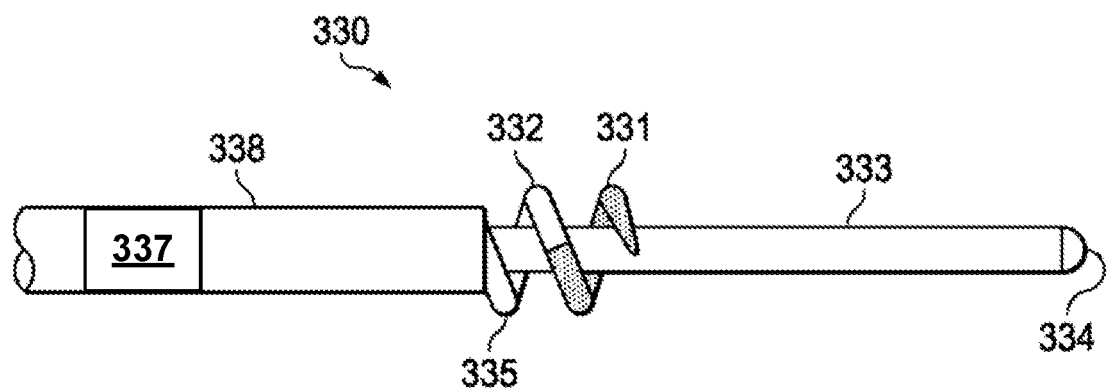
FIG. 9 illustrates an alternative lead design with a helix partially covered by an insulating layer.

FIG. 9 illustrates medical electrical lead 330. Lead 330 is substantially similar to lead 30 except that lead 330 includes an insulating layer 331 over the distal portion of helical electrode 332, partially covering helical electrode 332. The insulating layer 331 limits the exposed anode 335 surface area, increasing field density adjacent anode helical electrode 332 to allow for bifocal stimulation. In all other aspects, lead 330 is the same as lead 30. For brevity, details discussed with respect to lead 30 are discussed in limited or no detail with respect to lead 330.

Medical electrical lead 330 includes an anode ring electrode 337. Lead 330 also includes a central cable conductor 333 with blunt dissection electrode 334, and conductor for electrodes 332, 337. In some examples, the conductors for electrodes 332, 337 are coil conductor surrounding central cable conductor 333 within the lead body 338. In the same or different examples, the central cable conductor 333 may include an insulated conductor, such as a solid wire, a stranded wire, or a coil conductor.

Blunt dissection electrode 334 forms a rounded frontal surface extending across a width of the cable. In some examples, the blunt dissection electrode 334 is a 0.5 to 2 mm diameter, such as 0.7 to 1 mm diameter hemispherical electrode, such as a half sphere with a diameter of about 0.87 mm, at the end of an insulated blunt dissection electrode conductor of the same diameter in order to provide blunt dissection. In the same or different examples, the following materials may be utilized for the helical electrode 332 wire: Pt 80%/Ir 20% or Pt 90%/Ir 10% for a thinner wire. In the same or different examples, the insulating layer 331 over anode helical electrode 332 may be any suitable dielectric material, such as a polymer material, such as silicone rubber, polyurethane, parylene, polymide and/or ETFE or other non-conductive material.

The configuration of lead 330 provides reduced helical pacing current threshold compared to lead 30. Such a configuration may be particularly useful when right septal bifocal stimulation is desired for example. Such pacing may be useful to support LV/RV synchronization.

A ratio of anode to blunt dissection electrode surface area should be selected to support bipolar pacing. In some examples, the anode to blunt dissection electrode area ratio should be in 2:1 to 30:1, such as 4:1 to 20:1, such as about 16:1. In one particular example of lead 330 the following dimensions may be used. Lead 330 diameter 5 French, cable conductor 333 diameter 0.9 mm, helical electrode 332 length 1.8 mm, helical electrode 332 pitch 1 mm, helical electrode 332 wire diameter 0.3 mm, blunt dissection electrode 334 surface area 1.2 mm$^2$, exposed anode 335 surface area 20 mm$^2$.

Figure 10:
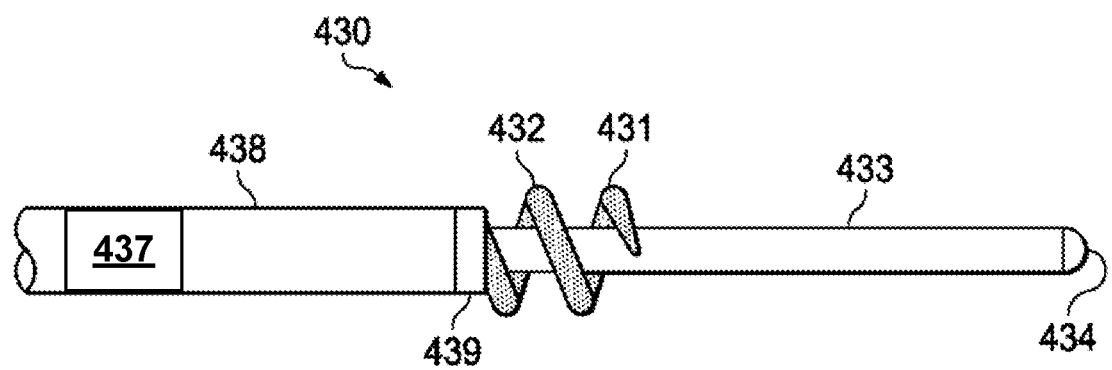
FIG. 10 illustrates an alternative lead design with an insulated helix fully covered by an insulating layer and a cathode ring on the distal end of the lead body.

FIG. 10 illustrates medical electrical lead 430. Medical electrical lead 430 includes an insulating layer 431 fully covering portion of helix 432. Medical electrical lead 430 further includes a ring electrode 439 on the distal end of lead body 438. In other examples, ring electrode 439 may be partial ring electrode. In the same or different examples, helix 432 is laser welded to ring electrode 439. In the same or different examples, ring electrode 439 may be on a distal portion of lead body 438, but not necessarily on the distal tip of lead body 438. Lead 430 is otherwise substantially similar to lead 30.

In the configuration of medical electrical lead 430, ring electrode 439 may serve as the second cathode and/or an anode to provide bipolar stimulation in combination with blunt dissection electrode 434. In all other aspects, lead 430 is the same as lead 30. For brevity, details discussed with respect to lead 30 are discussed in limited or no detail with respect to lead 430.

Medical electrical lead 430 includes an anode ring electrode 437 proximal to proximal to helix 432. Lead 430 also includes a central cable conductor 433 for a blunt dissection electrode 434, as well as a conductors for electrodes 437, 439. In some examples, the conductors for electrodes 437, 439 are coaxial, insulated coil conductors surrounding the central cable conductor 433 within the lead body 438. In the same or different examples, the central cable conductor 433 may include an insulated conductor, such as a solid wire, a stranded wire, or a coil conductor.

Blunt dissection electrode 434 forms a rounded frontal surface extending across a width of the cable. In some examples, the blunt dissection electrode 434 is a 0.5 to 2 mm diameter, such as 0.7 to 1 mm diameter hemispherical electrode, such as a half sphere with a diameter of about 0.87 mm, at the end of an insulated blunt dissection electrode conductor of the same diameter in order to provide blunt dissection. In the same or different examples, the following materials may be utilized for the helix 432 wire: Pt 80%/Ir 20% or Pt 90%/Ir 10% for a thinner wire. In the same or different examples, the helix coating 431 may be any suitable dielectric material, such as a polymer material, such as parylene, polymide or other non-conductive material.

Like lead 330, the configuration of lead 430 provides reduced helical current pacing threshold compared to lead 30. Such a configuration may be particularly useful when right septal bipolar stimulation is desired for example. A ratio of anode (such as ring electrode 439) to blunt dissection electrode surface area should be selected to support bifocal pacing. In some examples, the anode to blunt dissection electrode area ratio should be in 2:1 to 30:1, such as 4:1 to 20:1, such as about 16:1.

Such pacing may be useful to support LV/RV synchronization. For example, cathodal voltage stimulation of the LBB via blunt dissection electrode 434 and cathodal voltage stimulation of the RBB via electrode 439 can be independently adjusted to suit the LBB pacing voltage threshold and the RBB pacing voltage threshold independently to produce LV/RV synchrony. Alternatively, lead 430 may be operated to provide dual bifocal stimulation. In one example, the dual bifocal stimulation may operate ring electrode 437 as the anode and alternatively using blunt dissection electrode 434 and ring electrode 439 as cathodes. In another example, the dual bifocal stimulation may operate ring electrode 437 as the anode with and blunt dissection electrode 434 as the cathode alternated with operating ring electrode 437 as the anode with and ring electrode 439 as the cathode.

The configuration of lead 430 is also suitable for His bundle pacing near the endocardial surface by prevention of blunt dissection electrode shorting to the helical electrode as may occur with lead 30. Specifically, the location of ring electrode 439 provides further separation between ring electrode 439 and distal blunt dissection electrode 434 by the endocardial membrane. Such a configuration may mitigate short circuiting of the electrodes even with a shallow blunt dissection electrode placement. Such placement may be particularly useful when the His bundle presents near the endocardium as a shallow blunt dissection electrode placement would position the blunt dissection electrode adjacent the His bundle.

Figure 11:
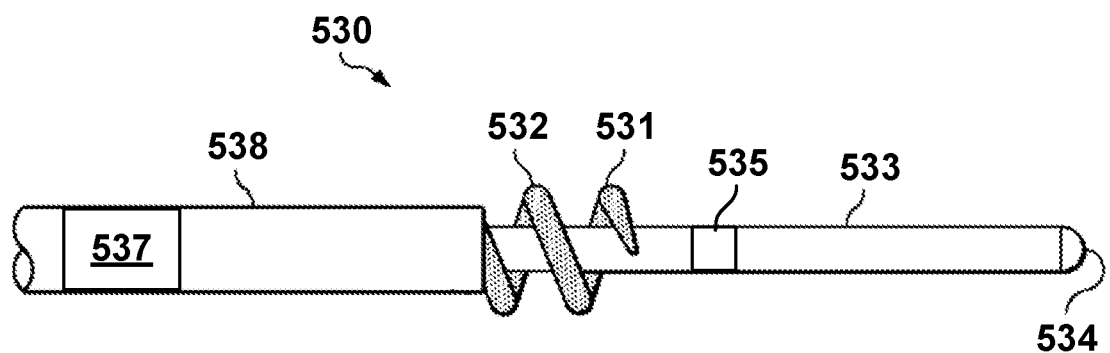
FIG. 11 illustrates an alternative lead design including two cable electrodes.

FIG. 11 illustrates medical electrical lead 530. Medical electrical lead 530 includes a ring electrode 535 on the cable conductor 533. Medical electrical lead 530 also includes an optional insulating layer 531 fully covering portion of helix 532. Lead 530 is otherwise substantially similar to lead 30.

In the configuration of medical electrical lead 530, ring electrode 535 may serve as the second cathode and/or an anode to provide bifocal stimulation in combination with blunt dissection electrode 534. In all other aspects, lead 530 is the same as lead 30. In addition, central cable conductor 533 includes two conductors, one for ring electrode 535, and one for blunt dissection electrode 534. For brevity, details discussed with respect to lead 30 are discussed in limited or no detail with respect to lead 530.

Medical electrical lead 530 includes an anode ring electrode 537 proximal to helix 532. Lead 530 also includes a central cable conductor 533 for a blunt dissection electrode 534 and ring electrode 539. In such examples, central cable conductor 533 includes at least two insulated conductors and at least two proximal contacts. In some examples, the central cable conductor 533 including solid wire, stranded wire, or coiled conductor. In the same or different examples, the anode conductor is a coil conductor surrounding the central cable conductor 533 within the lead body 538.

Blunt dissection electrode 534 forms a rounded frontal surface extending across a width of the cable. In some examples, the blunt dissection electrode 534 is a 0.5 to 2 mm diameter, such as 0.7 to 1 mm diameter hemispherical electrode, such as a half sphere with a diameter of about 0.87 mm, at the end of an insulated blunt dissection electrode conductor of the same diameter in order to provide blunt dissection. In the same or different examples, the following materials may be utilized for the helix 532 wire: Pt 80%/Ir 20% or Pt 90%/Ir 10% for a thinner wire. In the same or different examples, the helix coating 531 may be any suitable dielectric material, such as a polymer material, such as parylene, polymide or other non-conductive material.

Like lead 330, the configuration of lead 530 provides reduced bipolar current pacing threshold compared to lead 30. Such a configuration may be particularly useful when right septal bifocal stimulation is desired for example. A ratio of anode (ring electrode 537) to blunt dissection electrode surface area should be selected to support bifocal pacing. In some examples, the anode to blunt dissection electrode area ratio should be in 2:1 to 30:1, such as 4:1 to 20:1, such as about 16:1.

Such pacing may be useful to support LV/RV synchronization. For example, if electrode 535 and blunt dissection electrode 534 are designed to have a similar pacing capture voltage, the LBB can be stimulated at the same time as the right septal myocardial (or right bundle if it were viable and in range of the anode) to promote LV/RV synchrony. Alternatively, lead 530 may be operated to provide dual bifocal stimulation. In one example, the dual bifocal stimulation may operate ring electrode 537 as the anode and alternatively using blunt dissection electrode 534 and ring electrode 535 as cathodes. In another example, the dual bifocal stimulation may operate ring electrode 535 as the anode with and blunt dissection electrode 534 as the cathode alternated with operating ring electrode 537 as the anode with and ring electrode 535 as the cathode.

In a variation of lead 530, helix 532 may include an uninsulated portion forming a helical electrode, such that lead 530 includes four different electrodes: 534, 535, 532 and 537, each connected to an individual electrode in the proximal lead connector, which may conform to the IS-4 standard. For example, cable conductor 533 may include two insulated conductors, one for each of electrodes 534, 535. In such an example, connection to the proximal connector may occur by ring or split ring contacts. The four electrodes 534, 535, 532 and 537 may be used in any combination to provide stimulation and/or sensing. Such flexibility may allow a clinician to adjusting electrode combinations and/or stimulation parameters to account for scarring or lead migration, not only at the time of implantation of such a lead, but also in the months and years following implantation without the need for surgical intervention.

In further examples, cable conductor 533 may include a plurality of ring electrodes, such as two to ten electrodes. In such examples, cable conductor 533 may include a corresponding number of insulated conductors extending to individual electrical contacts at the proximal end of cable conductor 533. In one example, the individual electrical contacts may include ring electrodes, and/or partial ring electrodes and an optional pin electrode. Including more electrodes in lead 530 and cable conductor 533 will generally require a larger lead diameter to account for the additional conductors. In any of the examples described with respect to lead 530, two or more electrodes may also share a conductor such that they are operated jointly to provide stimulation or sensing.

A number of modifications to the techniques described herein are within the spirit of this disclosure. For example, while the disclosed techniques are described with respect to selecting the trajectory of an electrode for His bundle pacing, LBB pacing and/or RBB pacing, the leads and other techniques disclosed herein may also be used for different target sites, for cardiac pacing and otherwise.

As another example, the disclosed techniques could be used with any pulse generator, whether it is in the pectoral pocket or in the right ventricle. In this manner, the transseptal pacing leads disclosed herein are suitable with any implantable pulse generator using any particular pacing programming therapies and/or cardiac sensing techniques.

Various examples of this disclosure have been described. These and other examples are within the scope of the following claims.

The invention claimed is:
1. A medical lead comprising:
a lead body;
a connector proximate to a proximal end of the lead body;
a helix extending from a distal end of the lead body, wherein the helix is configured to anchor to a patient tissue, and wherein the helix forms a helical electrode;
a ring electrode proximate to the distal end of the lead body; and
a cable within the lead body, the cable including a cable conductor, a cable electrode proximate a distal end of the cable conductor, and a blunt dissection tip at a distal end of the cable,
wherein the cable conductor is a solid wire or a stranded wire,
wherein the cable is slidable within the lead body to drive extension and retraction of the cable electrode along a trajectory extending from the distal end of the lead body, and
wherein, when the helix is anchored to the patient tissue, the blunt dissection tip is configured to blunt dissect the patient tissue along the trajectory extending from the distal end of the lead body and past a distal end of the helix through extension of the cable.

2. The medical lead of claim 1, wherein the cable is slidable within the lead body to extend the cable electrode at least 1.8 centimeters from the distal end of the lead body.

3. The medical lead of claim 1, further comprising:
a first conductor within the lead body connecting the helical electrode to a first electrode of the connector; and
a second conductor within the lead body connecting the ring electrode to a second electrode of the connector,
wherein the cable conductor connects the cable electrode to a third electrode of the connector.

4. The medical lead of claim 3, wherein the third electrode is a connector pin.

5. The medical lead of claim 3, wherein the blunt dissection tip is a hemispherical tip.

6. The medical lead of claim 1, wherein the blunt dissection tip forms a rounded frontal surface extending across a width of the cable.

7. The medical lead of claim 1, wherein the cable electrode has a diameter of between 0.5 millimeters and 2.0 millimeters.

8. The medical lead of claim 1, wherein the cable conductor is an insulated cable conductor.

9. The medical lead of claim 1, further comprising an insulating layer partially covering the helical electrode.

10. The medical lead of claim 1, further comprising a proximal connector including connector terminals electrically coupled to the helical electrode, the ring electrode, and the cable electrode.

11. The medical lead of claim 1, wherein the cable conductor has a cable conductor diameter of 0.51-1.27 millimeters (0.02 to 0.05 inches).

12. The medical lead of claim 11, wherein the lead body has a lead body diameter of 1-2 millimeters (0.039-0.079 inches).

13. The medical lead of claim 1,
wherein the connector includes a connector pin, wherein the connector pin is configured to electrically couple to the cable electrode via the cable conductor.

14. The medical lead of claim 1, wherein the ring electrode is attached to the lead body.

15. A method for implanting a medical lead, the medical lead including:
a lead body;
a connector proximate to a proximal end of the lead body;
a helix extending from a distal end of the lead body, wherein the helix is configured to anchor to a patient tissue, and wherein the helix forms a helical electrode;
a ring electrode proximate to the distal end of the lead body; and a cable within the lead body, the cable including a cable conductor, a cable electrode proximate a distal end of the cable conductor, and a blunt dissection tip at a distal end of the cable, wherein the cable conductor is a solid wire or a stranded wire, and wherein the cable is slidable within the lead body to drive extension and retraction of the cable electrode along a trajectory extending from the distal end of the lead body, the method comprising:

securing the helix of to the patient tissue proximate a target site; and extending the cable conductor from the lead body to deploy the cable electrode within the patient tissue past a distal end of the helix.

16. The method of claim 15, wherein extending the cable conductor from the lead body extends the cable electrode at least 1.8 centimeters from the distal end of the lead body.

17. The method of claim 15, wherein securing the helix of the medical lead to the patient tissue includes:

positioning a distal end of a catheter proximate the target site;

delivering a distal end of the medical lead proximate the target site via the catheter; and rotating the helix to anchor the helix to the patient tissue.

18. The method of claim 17, further comprising, after securing the helix, manipulating the catheter to set the trajectory for deploying the cable electrode within the patient tissue, wherein manipulating the catheter includes one or more of:

bending the catheter through pushing and pulling from a proximal location outside the body of the patient; and rotating the catheter.

19. The method of claim 15, wherein deploying the cable electrode within the patient tissue includes blunt dissection of the patient tissue with the cable electrode.

20. The method of claim 15, wherein the target site is a septum of the patient.

21. The method of claim 15, wherein deploying the cable electrode within the patient tissue comprises deploying the cable electrode within the patient tissue to contact a left bundle branch of the patient.

22. The method of claim 15, wherein the target site is a septum of the patient, wherein, with the helix is anchored to the patient tissue and the cable electrode deployed within the patient tissue, the cable electrode is proximal to a left bundle branch and a right bundle branch of the patient, and wherein, with the helix is anchored to the patient tissue and the cable electrode deployed within the patient tissue, the helical electrode is proximal to the right bundle branch.

23. The method of claim 15, wherein the cable conductor has a cable conductor diameter of 0.51-1.27 millimeters (0.02 to 0.05 inches).

24. The method of claim 23, wherein the lead body has a lead body diameter of 1-2 millimeters (0.039-0.079 inches).

25. The method of claim 15, wherein the ring electrode is attached to the lead body.

26. A medical lead comprising:

a lead body;

a connector proximate to a proximal end of the lead body;

a helix extending from a distal end of the lead body, wherein the helix is configured to anchor to a patient tissue;

a ring electrode proximate to the distal end of the lead body; and a cable within the lead body, the cable including a cable conductor, a first cable electrode proximate a distal end of the cable conductor, a second cable electrode proximal the first cable electrode and a blunt dissection tip at a distal end of the cable, wherein the cable conductor includes two solid or stranded wires, one coupled to the first cable electrode and another coupled the second cable electrode, wherein the cable is slidable within the lead body to drive extension and retraction of the first cable electrode and the second cable electrode along a trajectory extending from the distal end of the lead body, and wherein, when the helix is anchored to the patient tissue, the blunt dissection tip is configured to blunt dissect the patient tissue along the trajectory extending from the distal end of the lead body and past a distal end of the helix through extension of the cable.

27. The medical lead of claim 26, wherein the cable conductor has a cable conductor diameter of 0.51-1.27 millimeters (0.02 to 0.05 inches).

28. The medical lead of claim 27, wherein the lead body has a lead body diameter of 1-2 millimeters (0.039-0.079 inches).

29. The medical lead of claim 26, wherein the connector includes a connector pin, wherein the connector pin is configured to electrically couple to the first cable electrode via the cable conductor.

30. The medical lead of claim 26, wherein the ring electrode is attached to the lead body.

31. A method for implanting a medical lead, the medical lead including:

a lead body;

a connector proximate to a proximal end of the lead body, wherein the connector includes a connector pin;

a helix extending from a distal end of the lead body, wherein the helix is configured to anchor to a patient tissue, and wherein the helix forms a helical electrode;

a ring electrode proximate to the distal end of the lead body; and a cable within the lead body, the cable including a cable conductor, a cable electrode proximate a distal end of the cable conductor, and a blunt dissection tip at a distal end of the cable, wherein the cable conductor is a solid wire or a stranded wire, and wherein the cable is slidable within the lead body to extend and retract the cable electrode along a trajectory extending from the distal end of the lead body, the method comprising:

securing the helix of to the patient tissue proximate a target site;

extending the cable conductor from the lead body to deploy the cable electrode within the patient tissue;

after deploying the cable electrode within the patient tissue, cutting the cable; and electrically coupling the connector pin to the cable electrode via the cable conductor.

* * * * *